United States Patent
Kim et al.

(10) Patent No.: US 7,563,931 B2
(45) Date of Patent: *Jul. 21, 2009

(54) PROCESS FOR PREPARATION OF PHENETHYLAMINE DERIVATIVES

(75) Inventors: Keun-Sik Kim, Suncheon-si (KR); Kwang-Il Kim, Yeosu-si (KR); Ki-Byung Chai, Yeosu-si (KR)

(73) Assignee: Wyeth, Madison, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/708,283

(22) Filed: Feb. 20, 2007

(65) Prior Publication Data

US 2007/0149813 A1 Jun. 28, 2007

Related U.S. Application Data

(63) Continuation of application No. 10/797,705, filed on Mar. 9, 2004, now Pat. No. 7,179,944.

(60) Provisional application No. 60/453,583, filed on Mar. 11, 2003.

(51) Int. Cl.
C07C 209/48 (2006.01)
(52) U.S. Cl. .................................. 564/358
(58) Field of Classification Search ................. None
See application file for complete search history.

(56) References Cited

U.S. PATENT DOCUMENTS 4,535,186 A 8/1985 Husbands et al. ........... 564/336

FOREIGN PATENT DOCUMENTS

| JP | 62129257 A2 | 6/1987 |
| WO | WO00/59851 | 10/2000 |
| WO | WO02/50017 A1 | 6/2002 |

OTHER PUBLICATIONS

Klenke, et al., J. Org. Chem., 2001, 2480-2483, 66.
Metayer, Ann. Chim., 1949, 196-257, 4 (with a translation).
Takamizawa, Synlett., 2001, 1623-1625, 10.
Yardley, et al., J. of Medicinal Chem., 1990, 2899-2905, 33.

*Primary Examiner*—Brian J Davis
(74) *Attorney, Agent, or Firm*—Charles E. Lyon; Choate, Hall & Stewart, LLP

(57) ABSTRACT

A process for the preparation of a compound of formula I,

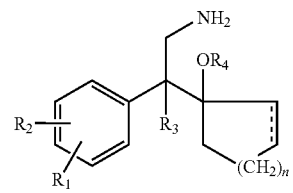

(I)

wherein $R_1$ and $R_2$ are ortho or para substituents, independently selected from the group consisting of hydrogen, hydroxyl, $C_1$-$C_6$ alkyl, $C_1$-$C_6$ alkoxy, $C_7$-$C_9$ aralkoxy, $C_2$-$C_7$ alkanoyloxy, $C_1$-$C_6$ alkylmercapto, halo and trifluoromethyl; $R_3$ is hydrogen or $C_1$-$C_6$ alkyl; $R_4$ is hydrogen, $C_1$-$C_6$ alkyl, formyl or $C_2$-$C_7$ alkanoyl; n is one of the integers 0, 1, 2, 3 or 4; and the dotted line represents optional olefinic unsaturation;

comprising hydrogenating a compound of formula III,

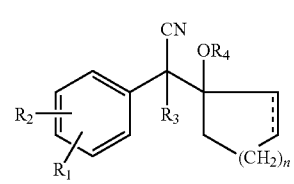

(III)

in the presence of a nickel or cobalt catalyst at a temperature of about 5° C. to 25° C.

11 Claims, No Drawings

PROCESS FOR PREPARATION OF PHENETHYLAMINE DERIVATIVES

This application claims priority to U.S. Ser. No. 10/797,705, filed on Mar. 9, 2004 (the '705 application, now U.S. Pat. No. 7,179,944, issued on Feb. 20, 2007); the present application is co-pending with and shares at least one common inventor with the '705 application. The present application is a continuation of the '705 application.

This application further claims priority to provisional application U.S. Ser. No. 60/453,583, filed on Mar. 11, 2003 (the '583 application); the '705 application was co-pending with and shared at least one common inventor with the '583 application. The '705 application claimed priority to the '583 application.

The entire disclosure of each of these applications is hereby incorporated by reference.

TECHNICAL FIELD

The present invention relates to an improved process for the preparation of phenethylamine derivatives by hydrogenation of phenylacetonitriles in the presence of a nickel or cobalt catalyst.

BACKGROUND

The compounds of formula I are useful intermediates for preparing pharmaceutically active substances, which have central nervous system anti-depressant effects by inhibiting re-uptake of the neurotransmitters, norepinephrine and serotonin. An example of such antidepressants is Venlafaxine (see Merck Index Twelfth Edition 1996, No. 10079). As disclosed in U.S. Pat. No. 4,535,186, the compounds of formula I can be produced by coupling a cycloalkanone or a cycloalkenone with an appropriately substituted phenylacetonitrils (step 1), and then catalytic hydrogenation of the coupled phenylacetonitriles (step 2). The present invention is related to an improvement of the second step reaction.

According to the preparation method disclosed in the '186 patent, the coupled phenylacetonitrile is hydrogenated over rhodium on alumina catalyst. However, the use of an Rh/Alumina catalyst is not desirable in terms of manufacturing costs, and thus, Rh/Alumina catalyst is not considered practical for industrial scale synthesis.

PCT WO 02/50017 discloses a process for preparation of phenethylamine derivatives by hydrogenation of phenylacetonitriles in the presence of a nickel or cobalt catalyst. Exemplification of PCT WO 02/50017 teaches a hydrogenation process carried out using a pretreated nickel or cobalt catalyst, for example, Raney nickel or Raney cobalt, in an organic solvent, such as alcohol, in the presence of a base, such as $NH_3$, $NH_4OH$, $NaOH$ at a temperature of 27° C. to 60° C.

A process employing a nickel or cobalt catalyst is considered to meet practical, economic considerations. However, some nickel or cobalt catalysts, for example, Raneyl nickel or Raney cobalt, are alkaline in their manufactured forms, and thus, require pretreatment with an acid, which is a cumbersome procedure. Furthermore, hydrogenation of nitrile compounds is usually conducted in a basic condition, such as an ammonia solution, because hydrogenation conducted in an acidic condition generally produces more undesired secondary or tertiary amines rather than desired primary amines as depicted in the scheme below, and the reaction may proceed slowly. In light of this, the pretreatment of a nickel or cobalt catalyst with an acid is not desirable.

It has been found that if hydrogenation of phenylacetonitriles in the presence of a nickel or cobalt catalyst is conducted under a basic condition at above room temperature such as those used in the process disclosed in PCT WO 02/50017, such a hydrogenation reaction results in cracking of the starting nitrile compounds to produce 4-methoxyphenylacetonitrile, which may be hydrogenated to produce 4-methoxyphenethylamine impurities, as shown below.

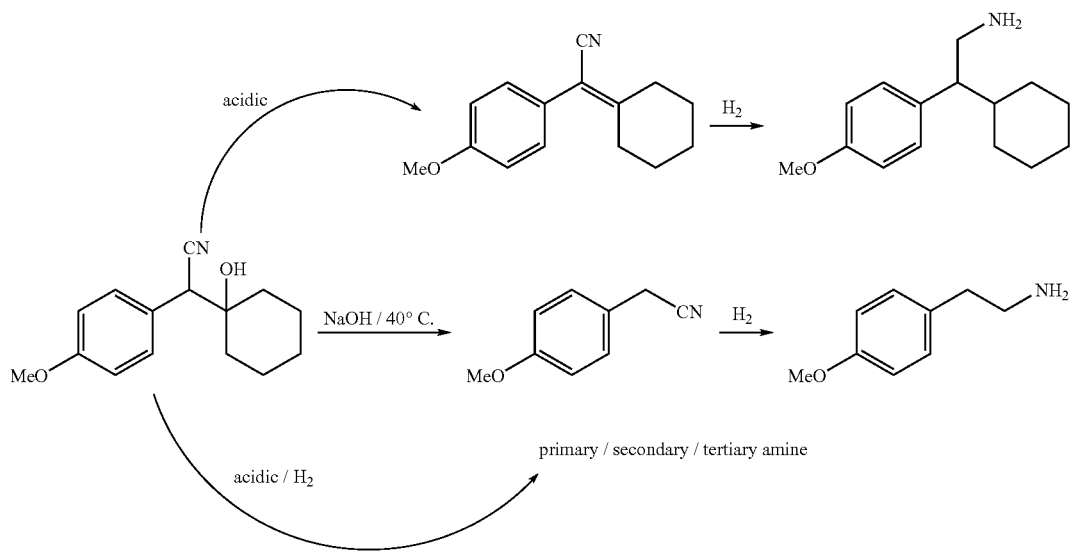

The present invention is based in part on a finding that hydrogenation of coupled phenylacetonitriles using a nickel or cobalt catalyst in a basic condition at a higher temperature produces substantial amounts of phenalkylamine impurities. The phenalkylamine impurities are very similar to the desired end products of primary amines in terms of physical and chemical properties, and thus, it is very difficult to separate them from the desired end products.

The improvement of reducing impurities, in particular, impurities that are difficult to separate, is an advantage over previously known processes.

SUMMARY

Accordingly, one of the objects of the present invention is directed to an improvement of a hydrogenation reaction using a nickel or cobalt catalyst to obtain high yield and purity compounds of formula (I), with decreased production of phenylalkylamine impurities such as 4-methoxyphenethylamine, by conducting the reaction at temperatures between about 5° C. and about 25° C.

Another object of the present invention is to provide a simplified process for the preparation of compounds of formula I in high yields and purity, which does not require pretreatment with an acid of a nickel or cobalt catalyst and is thus cost effective on an industrial scale.

A further object of the present invention is to provide an improved process for the preparation of phenethylamine compounds of formula (II) in high yields and purity.

DETAILED DESCRIPTION

One aspect of the present invention is to provide a process for the preparation of a compound of formula I,

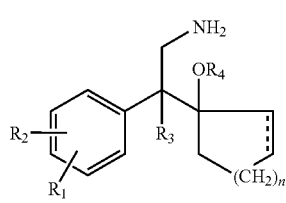

wherein $R_1$ and $R_2$ are ortho or para substituents, independently selected from the group consisting of hydrogen, hydroxyl, $C_1$-$C_6$ alkyl, $C_1$-$C_6$ alkoxy, $C_7$-$C_9$ aralkoxy, $C_2$-$C_7$ alkanoyloxy, $C_1$-$C_6$ alkylmercapto, halo or trifluoromethyl; $R_3$ is hydrogen or $C_1$-$C_6$ alkyl; $R_4$ is hydrogen, $C_1$-$C_6$ alkyl, formyl or $C_2$-$C_7$ alkanoyl; n is one of the integers 0, 1, 2, 3 or 4; and the dotted line represents optional olefinic unsaturation;

comprising hydrogenating a compound of formula III,

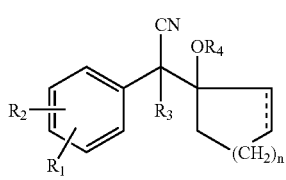

in the presence of a nickel or cobalt catalyst at a temperature of about 5° C. to about 25° C.

Another aspect of the present invention is to provide a process for preparing a compound of formula (II)

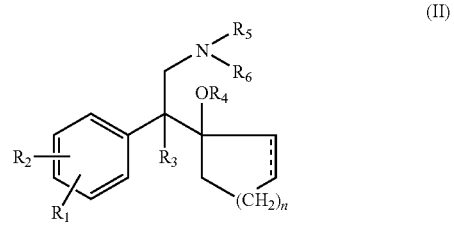

wherein $R_1$, $R_2$, $R_3$, $R_4$, n and the dotted line are as defined above; $R_5$ is hydrogen or $C_1$-$C_6$ alkyl and $R_6$ is $C_1$-$C_6$ alkyl;

comprising hydrogenating a compound of formula (III) in the presence of a nickel or cobalt catalyst at a temperature of about 5° C. to about 25° C. to produce a compound of formula (I) and alkylating the compound of formula (I).

The alkylation of a compound of formula (I) to a compound of formula (II) can be conducted by methods well known in the art. Such alkylation and the reaction conditions to be used are described in U.S. Pat. No. 4,535,186, incorporated by reference herein in its entirety Preferably, $R_1$ is hydrogen, hydroxy, $C_1$-$C_3$ alkoxy, chloro, bromo, trifluoromethyl or $C_1$-$C_3$ alkyl; $R_2$ is $C_1$-$C_3$ alkyl, $C_1$-$C_3$ alkoxy, chloro, bromo, trifluoromethyl or $C_2$-$C_3$ alkanoyloxy; $R_3$ is hydrogen or $C_1$-$C_3$ alkyl; $R_4$ is hydrogen; $R_5$ is hydrogen or $C_1$-$C_3$ alkyl and $R_6$ is $C_1$-$C_3$ an alkyl.

More preferably, $R_1$ and $R_2$ are in a para position, and n is 2.

The most preferred compounds of formula I are 1-[2-amino-1-(4-methoxy-phenyl)ethyl]cyclohexanol and 1-[2-amino-1-(4-hydroxy-phenyl)ethyl]cyclohexanol. The most preferred compounds of formula II are venlafaxine, O-desmethylvenlafaxine, N-desmethylvenlafaxine, N,N-didesmethylvenlafaxine, N,O-didesmethylvenlafaxine and O-desmethyl-N,N-didesmethylvenlafaxine.

In accordance with the present invention is provided compounds of Formula I substantially free of phenalkylamine impurities. In particular aspects of the invention the impurity is 4-methoxyphenethylamine or 4-hydroxyphenethylamine. Substantially free, as used herein, refers to greater than about 92% purity, more preferably greater than 95% purity and most preferably greater than 98% purity. Purity as used herein, refers to the absence of impurities, the majority of impurities, i.e. greater than 50%, being phenalkylamine impurities.

Nickel or cobalt catalysts to be used in the present invention are well known and commonly used in the art. Detailed information on nickel or cobalt catalysts are provided in WO 02/50017 A1, which is incorporated by reference in this application. The catalysts can be in supported or unsupported form. Typical support materials include, for example, carbon, aluminum oxide, silicium dioxide, $Cr_2O_3$, titanium dioxide, zirconium dioxide, zinc oxide, calcium oxide, magnesium oxide, barium sulfate, calcium carbonate or aluminum phosphate. The nickel or cobalt catalyst can be bound on the substrate in an amount of, for example, about 1.0 to about 20.0% by weight.

The preferred catalysts are Raney-Ni and Raney cobalt catalysts. Such catalysts are, for example, formed by mixing nickel and aluminum or cobalt and aluminum and subsequently treating the respective mixtures with a suitable base, such as sodium hydroxide to remove the aluminum, thus leaving a highly reactive nickel or cobalt metal catalyst.

In all cases, nickel catalysts are preferred; and highly preferred are Raney-Ni catalysts. Raney-Ni catalysts are commercially available from Grace, Degussa (for example, product No. B111 W, B112 W, B2112 Z), PMC (for example, product No. 5200, 5020, 5800), and AMC (for example, Product No. A-5000).

The amount of a nickel or cobalt catalyst to be used is not specifically limited and may be in the range from about 10% to about 50% by weight or more. Higher amounts of catalysts may be preferable in terms of activity and selectivity. However, reasonable amounts of catalysts are usually used in view of cost considerations. Catalyst is used in an amount of about 30% to 50% by weight, based on the amount of a compound of formula III.

The hydrogenation reaction of the present invention is preferably conducted in an organic solvent. An alcohol, such as MeOH, EtOH or isopropyl alcohol, is preferably used, MeOH is most preferable.

In the present invention, a basic compound such as ammonia may optionally be added to a reaction solution, which is advantageous to prevent production of impurities, such as secondary or tertiary amines, during the reduction process. Preferably, the amount of ammonia used is from 0.5 to about 1.5 equivalent, preferably from about 0.9 to about 1.1 equivalent, based on the weight of a compound of formula III.

In the present invention, the reaction temperature for the hydrogenation reaction is in the range of about 5° C. to about 25° C., preferably in the range of about 10° C. to 25° C., and more preferably in the range of about 15° C. to 20° C. If the temperature is more than about 25° C., the production of impurities is increased. If the temperature is less than about 5° C., the reaction rate becomes too slow.

A compound of formula (II) can be converted to a pharmaceutically acceptable salt. Said salts are prepared in accordance with procedures known to the art and may be formed conventionally by reaction of the free base with an equivalent amount of any acid which forms a non-toxic salt. Pharmaceutically acceptable inorganic or organic salts, include, but are not limited to, hydrochloric, hydrobromic, fumaric, maleic, succinic, tartarate, sulfuric, phosphoric, tartaric, acetic, and citric.

The present invention will now be described in detail with reference to the following examples, which are not intended to limit the scope of the present invention.

HPLC analysis was carried out under the following conditions:

Column: YMC Pack ODS AQ 4.6×250 mm
Mobile phase: 5 mM $KH_2PO_4$ 650 ml: $CH_3CN$ 350 ml: $H_3PO_4$ 1 ml
Detector: UV 220 nm
Flow rate: 1 ml/min
Sample concentration: 0.01 g/1 ml Eluent
Run time: 50 min

EXAMPLE 1

The reactor was charged with 25.0 g of Raney-Ni (Kawaken, Grace 2400, 2724, Degussa B111W, 112W), and 250 ml of MeOH and 25 ml of an ammonia solution (25% $NH_3$) were added. To the mixture was added 50g of 1-[cyano(4-methoxyphenyl)methyl]cyclohexanol, followed by 250 ml of MeOH. The reactor was settled and purged with $N_2$ gas two or three times. After fully purged with $N_2$, the reactor was purged with $H_2$ gas two or three times. Internal pressure of the reactor was adjusted to 60 psi and the reaction mixture was stirred. After 20 to 30 hours of reaction at room temperature (about 10 to 20° C.), in-process analysis of a sample of mixture was made. After the reaction was completed, Ra—Ni was removed by filtration with a celite pad. The filtrate was distilled under reduced pressure until all of the solvent was evaporated, and 200 ml of isopropyl alcohol and 400 ml of ethyl acetate were added to the residue oil to dissolve the resulting product to give a clear or a little hazy solution. To the solution was added 10 ml of acetic acid dropwise, and an exothermic reaction began with some fumes given off. After about 10 to 20 minutes of adding all of the acetic acid, a solid began to form. The solution was stirred for about one hour, filtered and washed with ethyl acetate to give the desired product, 1-[2-amino-1-(4-methoxyphenyl)ethyl]-cyclohexanol, 44.2 g (yield 70%, purity 99%).

HPLC analysis: desired product: 3.5 min; starting material: 35 min, 4-methoxyphenethylamine: 2.8 min, dehydrated compound: 8.5 min IR (KBr pellet): 3494 $cm^{-1}$, 3069, 2930, 2184, 1635, 1612, 1539

$^1H$ NMR Analysis (DMSO-$d_6$): δ 1.0-1.71 (m, 10H, cyclohexane), 1.818 (s, 3H, acetic acid), 2.72 (dd, 1H), 2.97 (t,1 H), 3.27 (dd, 1H), 3.73 (3H, s, $OCH_3$), 6.85 (d, 2H, aromatic), 7.15 (d, 2H, aromatic)

EXAMPLES 2 to 10

The tests were carried in the same manner as in Example 1, except the amounts of starting material, Raney-Ni and ammonia solution, the reaction temperature, and the reaction time as shown in the table below, and purities and yields of desired products were also shown in the end column of the table (r.t.=room temperature of about 10 to 20° C.).

| No. | 1-[cyano(4-methoxyphenyl)methyl] cyclohexanol(g) | Raney Ni (g) | Ammonia Solution (ml) | Reaction temperature (° C.) | Reaction Time(hr) | Purity (%) | Yield (%) |
|---|---|---|---|---|---|---|---|
| Ex. 2 | 7.0 | 3.5 | 3.5 | r.t. | 23 | 93.9 | 61 |
| 3 | 14.0 | 7.0 | 7.0 | r.t. | 21 | 97.1 | 73 |
| 4 | 14.0 | 7.0 | 7.0 | r.t. | 21 | 98.3 | 75 |
| 5 | 14.0 | 2.8 | 7.0 | r.t. | 22 | 99.5 | 60 |
| 6 | 7.0 | 1.4 | 7.0 | r.t. | 24 | 99.1 | 62 |
| 7 | 50.0 | 15 | 25 | r.t. | 22 | 98.6 | 63 |
| 8 | 50.0 | 15 | 25 | r.t. | 22 | 98.6 | 60 |
| 9 | 50.0 | 15 | 25 | r.t. | 23 | 98.6 | 61 |
| 10 | 50.0 | 15 | 25 | r.t. | 24 | 99.0 | 60 |

EXAMPLE 11

After 40 ml of $H_2O$ was added to a mass cylinder, the mass cylinder was placed on a balance. The balance was then zeroed. Raney-Ni was added to the mass cylinder and the increased volume of water was taken away while maintaining the total volume at 40 ml, until the total weight indicated by the balance was 12 g. $H_2O$ was removed and 40 g of fresh $H_2O$ was added in order to wash the catalyst. After washing, the $H_2O$ was removed. The reactor was charged with Raney-Ni while washing with 20 ml of $H_2O$ and 600 ml of MeOH. To the mixture was added 40 g of 1-[cyano(4-methoxyphenyl) methyl]cyclohexanol, followed by 20 ml of an ammonia solution. The reactor was settled, then purged with $N_2$ gas two or three times. After fully purged with $N_2$, the reactor was purged with hydrogen gas two or three times. The internal pressure of the reactor was adjusted to 60 psi, and then stirring was initiated. After 20 to 30 hours of reaction at room temperature, in-process analysis of a sample of mixture was made. After the reaction was completed, Ra—Ni was removed by filtration with a celite pad. The filtrate was distilled under a reduced pressure until all of the solvent was evaporated, and 160 ml of isopropyl alcohol and 320 ml of ethyl acetate were added to the residue oil and dissolved to give a clear or little hazy solution. To the solution was added 12 ml of acetic acid drop-wise. An exothermic reaction with some fumes began. After about 10 to 20 minutes of adding all of the acetic acid, a solid began to be produced. The solution was stirred for about one hour, filtered and washed with ethyl acetate to give the clear product, 1-[2-amino-1-(4-methoxyphenyl)ethyl]cyclohexanol, 35.3 g (yield 70%, purity 99%).

Comparative Examples 1 to 3

These comparative examples were carried in the same manner as those of Example 1, except the amounts of starting material, Raney-Ni and ammonia solution, the reaction temperature, and the reaction time as shown in the table below, and the purities and yields of the desired products are shown in the end column of the table.

While the present invention has been described with respect to the particular examples, it will be apparent to those skilled in the art that many changes and modifications may be made without departing from the scope of the invention as defined in the appended claims.

What is claimed is:
1. A process for the preparation of a compound of formula,

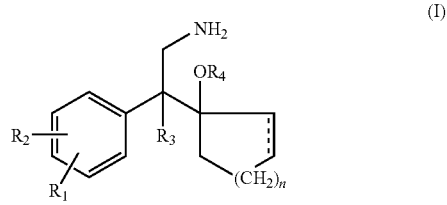

(I)

wherein $R_1$ and $R_2$ are ortho or para substituents, independently selected from the group consisting of hydrogen, hydroxyl, $C_1$-$C_6$ alkyl, $C_1$-$C_6$ alkoxy, $C_7$-$C_9$ aralkoxy, $C_2$-$C_7$ alkanoyloxy, $C_1$-$C_6$ alkylmercapto, halo and trifluoromethyl; $R_3$ is hydrogen or $C_1$-$C_6$ alkyl; $R_4$ is hydrogen, $C_1$-$C_6$ alkyl, formyl or $C_2$-$C_7$ alkanoyl; n is one of the integers 0, 1, 2, 3 or 4; and the dotted line represents optional olefinic unsaturation; comprising, hydrogenating a compound of formula III,

| No. | 1-[cyano(4-methoxyphenyl)methyl]cyclohexanol(g) | Raney Ni (g) | Ammonia Solution (ml) | reaction temperature (° C.) | Reaction Time(hr) | Purity* (%) | Major impurity** (%) |
|---|---|---|---|---|---|---|---|
| Com. Ex. 1 | 7.0 | 0.7 | 3.5 | 30 | 22 | 55.05 | 44.19 |
| Com. Ex. 2 | 7.0 | 3.5 | 3.5 | 25 | 22 | 52.07 | 39.04 |
| Com. Ex. 3 | 21.0 | 10.5 | 10.5 | 5 | 45 | 92.91 | 3.13 Reaction Not completed |

*Purity(%): content of 1-[2-amino-1-(4-methoxyphenyl)ethyl]cyclohexanol
**Major impurity(%): content of 4-methoxyphenethylamine

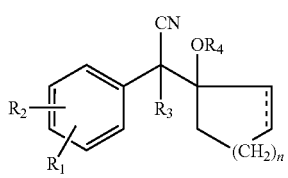

(III)

in the presence of a nickel or cobalt catalyst, at a temperature of about 10° C. to about 20° C.

2. The process of claim 1 wherein the catalyst is Raney-Ni.

3. The process of claim 1 wherein hydrogenation is carried out in the presence of methanol, ethanol or isopropyl alcohol.

4. The process of claim 1 wherein the amount of catalyst is from about 10 to about 50% by weight based on the amount of the compound of formula III.

5. The process of claim 4 wherein the amount of catalyst is from about 30 to about 50% by weight based on the amount of the compound of formula III.

6. The process of claim 1 wherein $R_1$ is hydrogen, hydroxyl, $C_1$-$C_3$ alkoxy, chloro, bromo, trifluoromethyl or $C_1$-$C_3$ alkyl; $R_2$ is $C_1$-$C_3$ alkyl, $C_1$-$C_3$ alkoxy, chloro, bromo, trifluoromethyl or $C_2$-$C_3$ alkanoyloxy; $R_3$ is hydrogen or $C_1$-$C_6$ alkyl; and $R_4$ is hydrogen.

7. The process of claim 1 wherein the compound of Formula I is 1-[2-amino-1-(4-methoxyphenyl)ethyl]cyclohexanol.

8. The process of claim 1 wherein the compound of Formula I is 1-[2-amino-1-(4-hydroxyphenyl)ethyl]cyclohexanol.

9. The process of claim 1 further comprising alkylating the compound of formula (I) to provide compound of Formula (II)

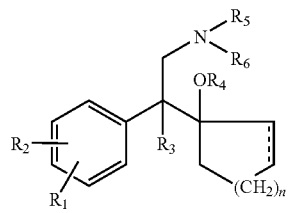

(II)

wherein $R_1$ and $R_2$ are ortho or para substituents, independently selected from the group consisting of hydrogen, hydroxyl, $C_1$-$C_6$ alkyl, $C_1$-$C_6$ alkoxy, $C_7$-$C_9$ aralkoxy, $C_2$-$C_7$ alkanoyloxy, $C_1$-$C_6$ alkylmercapto, halo and trifluoromethyl; $R_3$ is hydrogen or $C_1$-$C_6$ alkyl; $R_4$ is hydrogen, $C_1$-$C_6$ alkyl, formyl or $C_2$-$C_7$ alkanoyl; $R_5$ is hydrogen or $C_1$-$C_6$ alkyl; $R_6$ is $C_1$-$C_6$ alkyl; n is one of the integers 0, 1, 2, 3 or 4; and the dotted line represents optional olefinic unsaturation.

10. The process of claim 9, further comprising conversion of the compound of formula (II) to a pharmaceutically acceptable salt.

11. The process according to claim 10, wherein the compound of formula II is venlafaxine, O-desmethylvenlafaxine, N-desmethylvenlafaxine, N,N-didesmethylvenlafaxine, N,O-didesmethylvenlafaxine or O-desmethyl-N,N-didesmethylvenlafaxine, or a pharmaceutically acceptable salt thereof.

* * * * *